(12) United States Patent
Sata et al.

(10) Patent No.: US 8,349,024 B2
(45) Date of Patent: Jan. 8, 2013

(54) HAIR TREATMENT COMPOSITION

(75) Inventors: Juri Sata, Wakayama (JP); Tomoko Uchiyama, Wakayama (JP); Yoshinori Tamura, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/387,381

(22) PCT Filed: Sep. 28, 2010

(86) PCT No.: PCT/JP2010/067327
§ 371 (c)(1),
(2), (4) Date: Jan. 27, 2012

(87) PCT Pub. No.: WO2011/040632
PCT Pub. Date: Apr. 7, 2011

(65) Prior Publication Data
US 2012/0128615 A1    May 24, 2012

(30) Foreign Application Priority Data
Sep. 29, 2009    (JP) .................................. 2009-224197

(51) Int. Cl.
*A61Q 5/10*    (2006.01)
(52) U.S. Cl. ............. 8/405; 8/431; 8/435; 8/550; 8/561; 8/580; 8/611; 132/202; 132/208
(58) Field of Classification Search ............... 8/405, 431, 8/435, 550, 561, 580, 611; 132/202, 208
See application file for complete search history.

(56) References Cited

U.S. PATENT DOCUMENTS
6,312,677 B1    11/2001    Millequant et al.
2009/0124523 A1 *    5/2009    Dol et al. ........................ 510/119

2010/0069276 A1    3/2010    Inoue
2010/0222246 A1    9/2010    Doi et al.
2011/0014145 A1    1/2011    Sata et al.

FOREIGN PATENT DOCUMENTS

| EP | 1 142 560 | 10/2001 |
|---|---|---|
| EP | 2 062 567 | 5/2009 |
| JP | 1 106812 | 4/1989 |
| JP | 4 230614 | 8/1992 |
| JP | 7 267836 | 10/1995 |
| JP | 2003 286141 | 10/2003 |
| JP | 2007 145783 | 6/2007 |
| JP | 2007 211232 | 8/2007 |
| WO | 2007 052657 | 5/2007 |

OTHER PUBLICATIONS

STIC Search Report dated Jun. 12, 2012.*
International Search Report Issued May 10, 2011 in PCT/JP10/67327 Filed Sep. 28, 2010.

* cited by examiner

*Primary Examiner* — Eisa Elhilo
(74) *Attorney, Agent, or Firm* — Oblon, Spivak, McClelland, Maier & Neustadt, L.L.P.

(57) ABSTRACT

Provided is a hair treatment composition capable of imparting good manageability and excellent hair feel to the hair upon finishing permanent wave or hair dye treatment. The hair treatment composition has the following components (A) and (B): (A) a compound represented by the following formula (1): $R^1O-(PO)_n(EO)_m-R^2$ (1) wherein $R^1$ represents a linear or branched $C_{8-12}$ alkyl or alkenyl group, PO represents a propyleneoxy group, EO represents an ethyleneoxy group, n represents an average addition mole number and is from 1.5 to 5.0, m represents an average addition mole number and is from 0 to 1.0, and $R^2$ represents a hydrogen atom or a methyl group, and (B) at least one selected from keratin reducing agents, oxidizing agents, alkaline agents, and dyes for hair dye, wherein a content of an $R^1OH$ wherein $R^1$ represents a linear or branched $C_{8-12}$ alkyl or alkenyl group is 300 ppm or less.

25 Claims, No Drawings

HAIR TREATMENT COMPOSITION

CROSS REFERENCE TO RELATED APPLICATION

This application is a 371 of PCT/JP2010/067327, filed on Sep. 28, 2010, and claims priority to Japanese Patent Application No. 2009-224197, filed on Sep. 29, 2009.

FIELD OF THE INVENTION

The present invention relates to a hair treatment composition for a permanent wave agent or hair dye.

BACKGROUND OF THE INVENTION

There is a demand for the development of a hair cosmetic composition having a high conditioning effect because hair is prone to damage from chemical treatments such as coloring and permanent waving.

As a hair cosmetic composition having a high conditioning effect, there is conventionally known a hair cosmetic composition containing a polyoxyalkylene compound obtained by the addition polymerization of an alkylene oxide to a monohydric or polyhydric alcohol, and a crosslinking type polyacrylic acid polymer. It is the composition developed with a view to enhancing hair styling power, giving moisture to the hair, and providing moisturized, supple, and non-sticky hair (Patent Document 1).

There is also known a hair cosmetic composition containing an alkyl polyalkylene glycol ether, a cationic surfactant, and a fatty acid having a $C_{12-40}$ alkyl or alkenyl group. It is the composition developed with a view to improving the touch feeling of the damaged hair without giving stickiness or oily feeling to the hair (Patent Document 2).

Further, there is a report on a cosmetic composition to be used for the preparation of a dyeing or bleaching composition of keratin fibers. It contains (a) from 14 to 50% of a mixture of nonionic surfactants selected from linear or branched oxyethylenated and/or oxypropylenated and/or polyglycerolated fatty alcohols, the mixture being containing, at a predetermined proportion, at least one surfactant A with an HLB value not less than 14 according to the Griffin scale and a nonionic surfactant B with an HLB value not less than 1 but less than 10 according to the Griffin scale; and (b) from 0.05 to 10% of a cationic or amphoteric substantive polymer (Patent Document 3).

It is however impossible to satisfactorily prevent hair damage upon chemical treatments such as coloring or permanent waving.

On the other hand, it is disclosed that a detergent composition containing the following components (i) and (ii):

(i) a compound represented by the following formula (i):

wherein $R^1$ represents a linear or branched $C_{8-12}$ alkyl or alkenyl group, PO represents a propyleneoxy group, EO represents an ethylene oxy group, n means an average addition mole number and is from 1.5 to 3.0, m means an average addition mole number and is from 0 to 1.0, and $R^2$ represents a hydrogen atom or a methyl group, wherein the content of an alcohol represented by the formula (i) with n being 0, m being 0 and $R^2$ being a hydrogen atom is 3000 ppm or less, and (ii) a surfactant other than the component (i) is excellent in a foaming property (Patent Document 4).

PRIOR ART DOCUMENT

Patent Document
[Patent Document 1] JP-A-1-106812
[Patent Document 2] JP-A-4-230614
[Patent Document 3] JP-A-7-267836
[Patent Document 4] JP-A-2007-211232

SUMMARY OF THE INVENTION

The present invention provides a hair treatment composition having the following components (A) and (B):

(A) a compound represented by the following formula (1):

wherein $R^1$ represents a linear or branched $C_{8-12}$ alkyl or alkenyl group, PO represents a propyleneoxy group, EO represents an ethyleneoxy group, n represents an average addition mole number and is from 1.5 to 5.0, m represents an average addition mole number and is from 0 to 1.0, and $R^2$ represents a hydrogen atom or a methyl group, and (B) at least one member selected from keratin reducing agents, oxidizing agents, alkaline agents, and dyes for hair dye, wherein a content of an $R^1$OH wherein $R^1$ represents a linear or branched $C_{8-12}$ alkyl or alkenyl group is 300 ppm or less.

The present invention also provides the use of, for a permanent wave agent or hair dye, a composition having the following component (A):

(A) a compound represented by the following formula (1):

wherein $R^1$ represents a linear or branched $C_{8-12}$ alkyl or alkenyl group, PO represents a propyleneoxy group, EO represents an ethyleneoxy group, n represents an average addition mole number and is from 1.5 to 5.0, m represents an average addition mole number and is from 0 to 1.0, and $R^2$ represents a hydrogen atom or a methyl group, wherein a content of an $R^1$OH wherein $R^1$ represents a linear or branched $C_{8-12}$ alkyl or alkenyl group is 300 ppm or less.

DETAILED DESCRIPTION OF THE INVENTION

An object of the present invention is to provide a hair treatment composition which can be applied to the hair easily and is excellent in the finish of the hair subjected to chemical treatment with a permanent wave agent or hair dye.

The present inventors have carried out an extensive investigation. As a result, it has been found that a hair treatment composition containing, in addition to permanent wave or hair dye components, a polyoxyethylene polyoxypropylene alkyl ether or polyoxypropylene alkyl ether that has a relatively short-chain alkyl group and has a smaller and limited number of polyoxyethylene units and polyoxypropylene units, and having a reduced content of a raw material alcohol is excellent in good manageability and good feel imparting effects to the hair that has been subjected to chemical treatment such as hair coloring or perming, leading to the completion of the present invention. The reason of such effects has not been elucidated but when hair is chemically treated, the above-described compound easily penetrates into the hair. Therefore, it can enhance the hair conditioning effect without adversely affecting the performance such as hair dyeing properties.

Using the hair treatment composition of the present invention facilitates application of the component (A) to the hair and can impart good manageability and excellent feeling to the touch to the hair upon finishing of permanent waving or hair dyeing treatment.

The present invention will hereinafter be described more specifically.

In the formula (1) representing the component (A), $R^1$ is a linear or branched alkyl or alkenyl group having from 8 to 12, preferably from 8 to 10, more preferably 8 carbon atoms. From the standpoint of odor reduction, the linear or branched alkyl group is preferred. From the standpoints of odor reduction and manageability of hair, $R^1$ having 8 carbon atoms is preferred. In the case of a mixed alkyl group, it contains preferably an alkyl group with 8 carbon atoms in an amount of 50 mol % or greater, more preferably 80 mol % or greater, even more preferably 98 mol % or greater. When the number of carbon atoms of $R^1$ exceeds 12, the resulting hair treatment composition is excellent in suppleness (lack of stiffness) of the hair, but is not preferred because of inferior manageability of hair and an increased oily feel transferred to hands. When the number of carbon atoms is less than 8, on the other hand, the resulting hair treatment composition is sometimes inferior in manageability of the hair. When the number of carbon atoms of $R^1$ is from 8 to 10, the resulting composition is particularly excellent in manageability of hair. The reason why the hair treatment composition of the present invention is excellent in both an oily feel transferred to hands and manageability of the hair is presumed to be that the component (A) has both properties derived from the surfactant and the oily component.

In the formula (1) representing the component (A), PO and EO may be arranged either in blocks or at random, but the former one is preferred. From the standpoint of odor reduction, $(PO)_n$ and $(EO)_m$ are more preferably (added) arranged in blocks in the order of mention.

In the compound of the formula (1) as the component (A), the average addition mole numbers n and m are restricted in consideration of the balance between odor and manageability of hair. Described specifically, when the average addition mole numbers n and m are small, the content of a raw material alcohol increases, leading to increase in odor and reduction in manageability of hair. On the other hand, when the average addition mole numbers n and m are large, the resulting composition spreads well when it is applied to the hair, but is not preferred because of inferiority in manageability of the hair and oily feel transferred to hands.

From the standpoints of odor, spreadability upon application, oily feel transferred to hands, moisturized feel, manageability of the hair, and suppleness (lack of stiffness) of the hair, the average addition mole number n is from 1.5 to 5.0, preferably from 1.5 to 3.0, more preferably from 2.0 to 3.0, even more preferably from 2.2 to 2.8.

From the standpoints of spreadability upon application, manageability of the hair, and suppleness (lack of stiffness) of the hair, the average addition mole number m is from 0 to 1.0, preferably from 0 to 0.5, more preferably 0.

In addition, n+m is preferably from 1.5 to 4.0, more preferably from 1.5 to 3.0, even more preferably from 2.0 to 2.8 from the standpoints of odor, spreadability upon application, oily feel transferred to hands, manageability of the hair, and suppleness (lack of stiffness) of the hair.

Since the average addition mole numbers n and m in the formula (1) are average, the number of moles in each molecule has a distribution. With respect to the distribution of PO addition mole number in those mole numbers, a total proportion of compounds having 2 and 3 mole of PO addition mole number based on compounds having 1 to 5 mole of PO addition mole number contained in the component (A) is preferably from 58 to 80 mol %, more preferably from 60 to 70 mol % from the standpoints of oily feel transferred to hands and manageability of the hair.

Further, from the standpoints of oily feel transferred to hands, moisturized feel, manageability of the hair, and production ease, a proportion of a compound having a PO addition mole number of 1 is preferably from 10 to 25 mol %; a proportion of a compound having a PO addition mole number of 2 is preferably from 34 to 40%, a proportion of a compound having a PO addition mole number of 3 is preferably from 20 to 30 mol %, a proportion of a compound having a PO addition mole number of 4 is preferably from 9 to 18 mol %, and a proportion of a compound having a PO addition mole number of 5 is preferably from 3 to 9 mol %, each in compounds having a PO addition mole number of from 1 to 5 contained in the component (A).

The average addition mole number n and m can be determined from $^1$H-NMR. The distribution of the PO addition mole number can be determined by gas chromatography which will be described later. Even if EO is added, the above-described values are determined while paying attention to compounds having only PO added thereto.

In the formula (1), $R^2$ represents a hydrogen atom or a methyl group, with a hydrogen atom being preferred from the standpoint of productivity of the component (A).

In the hair treatment composition of the present invention, a compound represented by $R^1OH$, that is, a compound represented by the formula (1) with n being 0, m being 0, and $R^2$ representing a hydrogen atom, and having as $R^1$ a linear or branched $C_{8-12}$ alkyl or alkenyl group, preferably a compound represented by $R^1OH$ with $R^1$ representing a linear or branched $C_{8-10}$ alkyl or alkenyl group is contained in an amount of 300 ppm or less, preferably 150 ppm or less, more preferably 80 ppm or less, still more preferably 50 ppm or less, even more preferably 30 ppm or less from the standpoints of odor reduction, suppleness (lack of stiffness) of the hair, and manageability of the hair. Although there is no lower limit, the content is preferably 1 ppm or greater from the standpoint of production ease of the component (A).

The $R^1OH$ contained in the hair treatment composition of the present invention is derived from $R^1OH$ contained in the component (A). When in the formula (1) representing the component (A), $R^1$ has from 8 to 10 carbon atoms, the number of carbon atoms of $R^1$ of $R^1OH$ contained in the hair treatment composition is also from 8 to 10. Accordingly, in order to reduce the $R^1OH$ content to 300 ppm or less, it is preferred to reduce the content of the raw material alcohol by distilling off the raw material alcohol from the component (A).

In order to adjust the content of $R^1OH$ to fall within the above range, a compound having a low $R^1OH$ content may be used as the component (A) as will be described later. The raw material alcohol for $R^1OH$ may be removed from the composition after preparing the component (A), but the former method can reduce the content more efficiently.

The component (A) is added in an amount of preferably 0.1% by weight or greater, more preferably 0.5% by weight or greater, even more preferably 1% by weight or greater, even more preferably 1.5% by weight or greater from the standpoint of improving the spreadability upon application, manageability of the hair, and suppleness (lack of stiffness) of the hair. Further, the amount is preferably 10% by weight or less, more preferably 7% by weight or less, even more preferably 5% by weight or less, still more preferably 4% by weight or less from the standpoint of improving the oily feel transferred to hands, the suppleness (lack of stiffness) of the hair, manageability of the hair, and dyeing properties. In consideration of these points totally, the component (A) is contained in the hair treatment composition in an amount of preferably from 0.1 to 10% by weight, more preferably from 0.5 to 7% by weight, even more preferably from 0.5 to 5% by weight, even more preferably from 1 to 5% by weight, still more preferably from 1.5 to 4% by weight.

A compound represented by $R^1OH$, that is, a compound represented by the formula (1) with n being 0, m being 0, and $R^2$ representing a hydrogen atom, and having as $R^1$ a linear or branched $C_{8-12}$ alkyl or alkenyl group, preferably a compound represented by $R^1OH$ with $R^1$ representing a linear or branched $C_{8-10}$ alkyl or alkenyl group is contained in the component (A) in an amount of preferably 3000 ppm or less, more preferably 2000 ppm or less, even more preferably 1500 ppm or less, even more preferably 1000 ppm or less, even more preferably 500 ppm or less from the standpoints of odor reduction, spreadability upon application, suppleness (lack of stiffness) of the hair, and manageability of the hair. The amount of $R^1OH$ can be reduced by distillation or the like as will be described later.

The component (A) to be used in the present invention can be obtained by reacting a raw material alcohol represented by $R^1OH$ (wherein $R^1$ represents a linear or branched alkyl or alkenyl group having from 8 to 12 carbon atoms, preferably from 8 to 10 carbon atoms) with propylene oxide or propylene oxide and ethylene oxide in the presence of a basic catalyst and then distilling off the raw material alcohol. The average addition mole number of propylene oxide or ethylene oxide to be added upon reaction are preferably the above-described values of n, m, and n+m.

Accordingly, the $R^1OH$ contained in the component (A) is derived from the raw material alcohol and when in the formula (1) representing the component (A), $R^1$ has from 8 to 10 carbon atoms, the number of carbon atoms of $R^1$ of $R^1OH$ contained in the component (A) is also from 8 to 10.

As the basic catalyst, potassium hydroxide, sodium hydroxide, lithium hydroxide, sodium alkoxide, or the like is used. It is added in an amount of preferably from 0.1 to 5 mol %, more preferably from 0.1 to 2 mol %, each based on the raw material alcohol represented by $R^1OH$. The reaction temperature is preferably from 80 to 200° C., more preferably from 110 to 160° C. and the reaction pressure is preferably from 0.1 to 0.8 MPa, more preferably from 0.1 to 0.6 MPa.

The reaction product may be subjected to distillation as is or it may also be subjected to distillation after removal of the basic catalyst by using a neutralizing agent, adsorbent, or the like. The term "distilling off the raw material alcohol" means that the raw material alcohol is removed by distillation or steam treatment or removed by using distillation and steam treatment in combination. The term "steam treatment" means a treatment of blowing steam to the reaction composition and distilling off the raw material alcohol from the system together with the steam. The distillation is performed under the following conditions.

Temperature: from 80 to 200° C., preferably from 80 to 150° C.

Pressure: 27 kPa (200 torr) or less, preferably 6 kPa (45 torr) or less

Amount of steam: from 0 to 50 parts by weight based on 100 parts by weight of the reaction composition.

The hair treatment composition according to the present invention contains further as the component (B) one or more member selected from a keratin reducing agent, an oxidizing agent, an alkaline agent and a dye for hair dye and is used as a permanent wave agent or hair dye. A weight ratio of the component (A) to the component (B) [the component (A)/the component (B)] is preferably from 1/10 to 10/1, more preferably from 1/7 to 5/1, even more preferably from 1/5 to 3/1 from the standpoints of enhancing hair conditioning effects and providing the hair with excellent manageability while keeping the performance of the component (B).

<Permanent Wave Agent>

The permanent wave agent of the present invention contains a hair relaxer.

The permanent wave agent of the present invention can be obtained as a first-part or second-part agent by mixing the component (A) with one or more member selected from a keratin reducing agent and oxidizing agent.

(Keratin Reducing Agent)

A keratin reducing agent can cause cleavage of disulfide bonds of keratin constituting the hair. Such a hair treatment composition can be used preferably as a first-part permanent wave agent.

In this case, the keratin reducing agent is preferably thioglycolic acid or derivative thereof, thiolactic acid or derivative thereof, cysteine or derivative thereof, or salt thereof, a thioglyceryl alkyl ether represented by the following formula (2):

$$R^3OCH_2CH(OH)CH_2SH \quad (2)$$

wherein $R^3$ represents a hydrogen atom, a lower alkyl group, or a lower alkoxy lower alkyl group, or salt thereof, and a mercaptoalkylamide represented by the following formula (3):

$$H-(CHOH)_x-(CH_2)_y-CONH(CH_2)_z-SH \quad (3)$$

wherein x stands for a number from 0 to 5, y stands for a number from 0 to 3, and z stands for a number from 2 to 5, with the proviso that y and z do not simultaneously stand for 0, or salt thereof. Preferred examples include thioglycolic acid, thioglycolic acid esters, thiolactic acid, thiolactic acid esters, cysteine, N-acylcysteines, compounds represented by the formula (2), and compounds represented by the formula (3), and salts thereof. Specific examples include thioglycolic acid, glycerol thioglycolate, L-cysteine, D-cysteine, and N-acetylcysteine, ammonium salts and ethanolamines salts such as monoethanolamine, diethanolamine, and triethanolamine of these cysteines, thioglyceryl alkyl ethers such as ethoxyhydroxypropanethiol, methoxyethoxyhydroxypropanethiol, and isopropoxyethoxyhydroxypropanethiol, (mercaptoethyl)propanamide, and (mercaptoethyl)gluconamide or the like.

The content of the keratin reducing agent in the hair treatment composition ranges preferably from 0.1 to 20% by weight, more preferably from 1 to 5% by weight. When the content of the keratin reducing agent is excessively small, sufficient reduction of keratin cannot be achieved. On the other hand, when the content is excessively large, effects proportionate to the amount cannot be obtained.

In this case, the pH of the hair treatment composition is adjusted to from 3.0 to 9.5, more preferably from 4.0 to 9.0 in order to suppress the damage of the skin or hair. The adjustment of the pH can be performed with a known pH regulator.

(Oxidizing Agent)

An oxidizing agent is mixed with the second-part agent of the permanent wave agent to be used in combination with the first-part agent of the permanent wave agent described above. Examples of the oxidizing agent include potassium bromate, sodium bromate, sodium perborate, and hydrogen peroxide or the like.

Such an oxidizing agent is incorporated in the hair treatment composition in an amount of preferably from 1 to 20% by weight, more preferably from 2 to 10% by weight. This can sufficiently reform the disulfide bonds of keratin in the hair which have once been broken.

The permanent wave agent according to the present invention can contain, in addition to the above-described components, components ordinarily employed for the same intended use as needed. Examples of such optional components include alkaline agents, surfactants, oil components, solubilizing agents, buffers, stabilizers, fragrances, colorants, antiseptics, pH regulators, thickeners, hair protecting agents, UV rays protective ingredients, anti-inflammatory agents, moisturizing agents, touch improvers, astringents, chelating agents, and hair growth components or the like.

The permanent wave agent of the present invention can be applied to any form such as one-part agent, a two-part agent having a first-part agent composed mainly of a reducing agent and a second-part agent composed mainly of an oxidizing agent, an agent to be used at room temperature, an agent to be used after heating, an agent for forming waves, and an agent for relaxing curly hair. The component (A) described above may be added to either of the keratin reducing agent or the oxidizing agent.

<Hair Dye>

In the present invention, the term "hair dye" embraces, in addition to a hair dying agent containing a dye, a hair decolorizing agent not containing a dye. The term "dyeing" means, in addition to simply dyeing hair with a hair dye containing a dye, decolorizing the hair and dyeing the decolorized hair, and decolorizing the hair with a decolorizing agent not containing a dye.

The hair dye of the present invention contains (A) the component described above and (B) one or more member selected from an oxidizing agent, an alkaline agent and a dye for hair dye.

The hair dye of the present invention contains both a one-part type and a multi-part type. The term "one-part" composition means a composition composed of a single agent and examples of such a form include:
1) a one-part hair dye containing a direct dye and, if necessary, an oxidizing agent, and
2) a one-part hair dye containing an oxidizing agent but not a dye.

On the other hand, the term "multi-part" composition means a composition composed of two or more agents and examples of such a form include:
3) a two-part hair dye composed of a first-part agent containing an alkaline agent and a dye and a second-part agent containing an oxidizing agent, and
4) a three-part hair dye composed of a first-part agent containing an alkaline agent, a second-part agent containing an oxidizing agent, and a third-part agent containing an oxidizing aid.

In the present invention, the one-part hair dye may contain the component (A) and an oxidizing agent or a dye, and the multi-part hair dye may contain the component (A) and an alkaline agent, an oxidizing agent or a dye.

<Dye>

In the multi-part hair dye composition, a direct dye and/or oxidation dye intermediate can be incorporated in the first-part agent. The dye for hair dye contains a direct dye and an oxidation dye intermediate.

Examples of the direct dye include nitro dyes, anthraquinone dyes, acid dyes, oil soluble dyes, and basic dyes or the like.

Examples of the nitro dyes include HC Blue NO. 2, HC Orange No. 1, HC Red No. 1, HC Red No. 3, HC Yellow No. 2, and HC Yellow No. 4 or the like.

Examples of the anthraquinone dye include 1-amino-4-methylaminoanthraquinone and 1,4-diaminoanthraquinone or the like.

Examples of the acid dye include Red No. 2, Red No. 3, Red No. 102, Red No. 104, Red No. 105, Red No. 106, Red No. 201, Red No. 227, Red No. 230, Red No. 232, Red No. 401, Red No. 502, Red No. 503, Red No. 504, Red No. 506, Orange No. 205, Orange No. 206, Orange No. 207, Yellow No. 4, Yellow No. 5, Yellow No. 202, Yellow No. 203, Yellow No. 402, Yellow No. 403, Yellow No. 406, Yellow No. 407, Green No. 3, Green No. 201, Green No. 204, Green No. 205, Green No. 401, Green No. 402, Blue No. 1, Blue No. 2, Blue No. 202, Blue No. 205, Violet No. 401, Black No. 401, Acid Blue 1, Acid Blue 3, Acid Blue 62, Acid Black 52, Acid Brown 13, Acid Green 50, Acid Orange 6, Acid Red 14, Acid Red 35, Acid Red 73, Acid Red 184, and Brilliant Black 1 or the like.

Examples of the oil-soluble dye include Red No. 215, Red No. 218, Red No. 225, Orange No. 201, Orange No. 206, Yellow No. 201, Yellow No. 204, Green No. 202, Violet No. 201, Red No. 501, Red No. 505, Orange No. 403, Yellow No. 404, Yellow No. 405, and Blue No. 403 or the like.

Examples of the basic dyes include Basic Blue 6, Basic Blue 7, Basic Blue 9, Basic Blue 26, Basic Blue 41, Basic Blue 99, Basic Brown 4, Basic Brown 16, Basic Brown 17, Basic Green 1, Basic Red 2, Basic Red 12, Basic Red 22, Basic Red 51, Basic Red 76, Basic Violet 1, Basic Violet 3, Basic Violet 10, Basic Violet 14, Basic Violet 57, Basic Yellow 57, Basic Yellow 87, and Basic Orange 31 or the like.

Of these, the acid dyes are preferred, with Yellow No. 4, Yellow No. 203, Yellow No. 403, Orange No. 205, Green No. 3, Green No. 201, Green No. 204, Red No. 2, Red No. 104, Red No. 106, Red No. 201, Red No. 227, Blue No. 1, Blue No. 205, Violet No. 401, and Black No. 401 being more preferred.

One or more of these direct dyes can be used. The content of it (them) in the hair treatment composition of the present invention is preferably from 0.005 to 5% by weight, more preferably from 0.01 to 2% by weight.

As the oxidation dye intermediate, known precursors and couplers ordinarily used for hair dyes may be used.

Examples of the precursor include p-phenylenediamine, toluene-2,5-diamine, o-chloro-p-phenylenediamine, N-phenyl-p-phenylenediamine, N,N-bis(hydroxyethyl)-p-phenylenediamine, 3-methyl-4-aminophenol, 2-hydroxyethyl-p-phenylenediamine, p-aminophenol, p-methylaminophenol, 4-amino-m-cresol, and o-aminophenol, and salts thereof or the like.

Examples of the coupler include resorcin, 2-methylresorcin, 1-naphthol, 1,5-dihydroxynaphthalene, 5-amino-o-cresol, m-phenylenediamine, m-aminophenol, 2,4-diaminophenoxyethanol, 2,6-diaminopyridine, 2-methyl-5-hydroxyethylaminophenol, and 2-amino-3-hydroxypyridine, and salts thereof or the like. Two or more of these precursors or these couplers may be used in combination. The content of the precursor(s) or coupler(s) in the whole composition is preferably from 0.01 to 5% by weight, more preferably from 0.1 to 4% by weight.

(Alkaline Agent)

The hair dye of the present invention may contain an alkaline agent. A multi-part hair dye may contain, in the first-part agent thereof, the alkaline agent.

Examples of the alkaline agent include ammonia or salts thereof, alkanolamines such as monoethanolamine, isopropanolamine, 2-amino-2-methylpropanol, and 2-aminobutanol, and salts thereof, alkanediamines such as 1,3-propanediamine, and salts thereof, and carbonates such as guanidine carbonate, sodium carbonate, potassium carbonate, sodium hydrogen carbonate, and potassium hydrogen carbonate or the like. Of these, ammonia, alkanolamine, and salts thereof are more preferred.

Two or more of these alkaline agents may be used in combination. The content of it (them) in the whole composition is preferably from 0.05 to 15% by weight, more preferably from 0.1 to 10% by weight, even more preferably from 0.2 to 5% by weight from the standpoints of satisfactory dyeing properties/decolorizing property and reduction of hair damage or irritation of scalp.

(Oxidizing Agent)

The hair dye of the present invention may contain an oxidizing agent. When the hair dye is a multi-part type, it may contain, in the second-part agent thereof, the oxidizing agent.

Examples of the oxidizing agent include hydrogen peroxide, and generators of hydrogen peroxide or oxygen such as urea peroxide, melamine peroxide, sodium perborate, potassium perborate, sodium percarbonate, and potassium percarbonate. Of these, hydrogen peroxide is more preferred.

These oxidizing agents may be used either singly or in combination of two or more. The content of the oxidizing agent(s) in the whole composition is preferably from 0.1 to 12% by weight, more preferably from 0.5 to 9% by weight, still more preferably from 1 to 6% by weight from the standpoints of satisfactory hair dyeing/hair decolorizing effect and reduction in hair damage and irritation of scalp.

(Oxidizing Aid)

The multi-part hair dye of the present invention may contain, in the third-part agent thereof, an oxidizing aid.

As the oxidizing aid, oxidizing agents other than the above-described ones can be used. Examples include persulfates or the like. Specific example includes ammonium persulfate, potassium persulfate, and sodium persulfate or the like. These are provided preferably in the form of powders such as granulated powders.

These oxidizing aids may be used either singly or in combination of two or more. The content of the oxidizing aid(s) in the whole composition is preferably from 0.1 to 50% by weight, more preferably from 1 to 30% by weight, even more preferably from 3 to 25% by weight from the standpoints of satisfactory decolorizing effect and reduction in hair damage and irritation of scalp.

[Other Components]

The hair treatment composition of the present invention preferably contains at least one surfactant [Component (C)] selected from anionic surfactants, amphoteric surfactants, nonionic surfactants, and cationic surfactants from the standpoints of causing the component (A) to stick to the hair well and enhancing the effect of the composition.

As the above-described anionic surfactant, sulfate-, sulfonate-, carboxylate-, phosphate-, and amino acid-based surfactants are preferred. Examples include alkyl sulfates, polyoxyalkylene alkyl ether sulfates, polyoxyalkylene alkenyl ether sulfates, alkyl sulfosuccinates, polyoxyalkylene alkyl sulfosuccinates, polyoxyalkylene alkyl phenyl ether sulfates, alkane sulfonates, acyl isethionates, acyl methyl taurates, higher fatty acid salts, polyoxyalkylene alkyl ether acetates, alkyl phosphates, polyoxyalkylene alkyl ether phosphates, acyl glutamates, alanine derivatives, glycine derivatives and arginine derivatives or the like.

Examples of the amphoteric surfactants include betaine surfactants and amine oxide surfactants. Of these, betaine surfactants such as imidazoline betaines, alkyldimethylaminoacetic acid betaines, fatty acid amidopropyl betaines, and sulfobetaines and amine oxide surfactants such as alkyl dimethyl amine oxides are more preferred, with alkyl carboxymethyl hydroxyethyl imidazolium betaines, fatty acid amidopropyl betaines, sulfobetaines such as alkyl hydroxy sulfobetaines, alkyl sulfobetaines, fatty acid amidopropylhydroxy sulfobetaines, and fatty acid amidopropyl sulfobetaines, and alkyl dimethyl amine oxides being even more preferred.

As the cationic surfactant, quaternary ammonium salt cationic surfactants or tertiary amine cationic surfactants are preferred.

Examples of the quaternary ammonium salt cationic surfactants include mono(long-chain alkyl) ($C_{12-28}$) quaternary ammonium salts, di(long-chain alkyl) ($C_{12-28}$) quaternary ammonium salts, branched alkyl ($C_{12-28}$) quaternary ammonium salts, alkylamido ($C_{12-28}$) alkyl ($C_{1-5}$) quaternary ammonium salts, N-hydrocarbon ($C_{12-28}$) carbamoylalkyl ($C_{1-5}$) quaternary ammonium salts, acyl ($C_{12-28}$) oxyalkyl ($C_{1-5}$) quaternary ammonium salts, and alkyl or alkenyl ($C_{12-28}$) oxyalkyl ($C_{1-5}$) quaternary ammonium salts.

The mono(long-chain alkyl) ($C_{12-28}$) quaternary ammonium salts include stearyltrimethylammonium chloride, myristyltrimethylammonium chloride, cetyltrimethylammonium chloride, arachyltrimethylammonium chloride, behenyltrimethylammonium chloride, lauryltrimethylammonium chloride, and N-stearyl-N,N,N-tri(polyoxyethylene)ammonium chloride (3 moles addition in total) or the like.

The di(long-chain alkyl or alkenyl) ($C_{12-28}$) quaternary ammonium salts include distearyldimethylammonium chloride, dioleyldimethylammonium chloride, dipalmitylmethylhydroxyethylammonium methosulfate, diisostearyldimethylammonium methosulfate, di[(2-dodecanoylamino)ethyl] dimethylammonium chloride, and di[(2-stearoylamino) propyl]dimethylammonium ethosulfate or the like.

The branched alkyl ($C_{12-28}$) quaternary ammonium salts include 2-decyltetradecyltrimethylammonium chloride, 2-dodecylhexadecyltrimethylammonium chloride, di-2-hexyldecyldimethylammonium chloride, and di-2-octyldodecyldimethylammonium chloride or the like.

The alkylamido ($C_{12-28}$) alkyl ($C_{1-5}$) quaternary ammonium salts include stearamidopropyl quaternary ammonium salts. The N-hydrocarbon ($C_{12-28}$) carbamoylalkyl ($C_{1-5}$) quaternary ammonium salts include N-stearylcarbamoylpropyl quaternary ammonium salts. The acyl ($C_{12-28}$) oxyalkyl ($C_{1-5}$) quaternary ammonium salts include stearoylpropyl quaternary ammonium salts. The hydrocarbon ($C_{12-28}$) oxyalkyl ($C_{1-5}$) quaternary ammonium salts include octadecyloxypropyltrimethylammonium chloride.

Preferred specific examples of the tertiary amine compounds include N,N-dimethyloctadecyloxypropylamine and stearamidopropyldimethylamine or the like.

As the tertiary amine cationic surfactant, tertiary amine compounds may be used as is or acid addition salts thereof may be used. As an acid, an inorganic acid or an organic acid may be used.

Examples of the nonionic surfactant include polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers other than the component (A), polyoxyalkylene alkylphenyl ethers, polyoxyalkylene (hydrogenated) castor oils, sucrose fatty acid esters, polyglycerin alkyl ethers, polyglycerin fatty acid esters, and alkyl glycosides or the like. Of these, alkyl glycosides, polyoxyethylene ($C_{8-20}$) alkyl ethers (preferably, the average addition mole number of EO from 3 to 50), polyoxyethylene sorbitan fatty acid esters, polyoxyethylene hydrogenated castor oils, and fatty acid alkanolamides are preferred.

Two or more of these surfactants may be used in combination. The content of it (them) in the hair treatment composition is preferably from 0.1 to 10% by weight, more preferably from 0.3 to 7% by weight, still more preferably from 0.3 to 5% by weight from the standpoints of stability and feeling to the touch.

The composition of the present invention preferably contains (D) an oily component from the standpoint of enhancing manageability of the hair and suppleness (lack of stiffness) of the hair through the interaction with the component (A) while enabling stable mixing of the component (A) and suppressing transfer to hands.

Examples of the oily component include higher alcohols, silicones, ester oils, hydrocarbons, glycerides, plant oils, animal oils, lanolin derivatives, and higher fatty acid esters or the like. From the above-described standpoint, higher alcohols, ester oils, and/or silicones are preferred, of which higher alcohols and/or silicones are more preferred and higher alcohols are even more preferred.

Examples of the higher alcohols include higher alcohols having a linear or branched alkyl or alkenyl group. The higher alcohols having a linear or branched alkyl or alkenyl group have preferably from 16 to 26 carbon atoms, more preferably from 16 to 22 carbon atoms. Even more preferred examples include higher alcohols such as cetanol, cetyl alcohol, stearyl alcohol, arachyl alcohol, behenyl alcohol, carnaubyl alcohol, ceryl alcohol, oleyl alcohol, and isostearyl alcohol, with one or more, as a mixture, of cetanol, cetyl alcohol, stearyl alcohol, and behenyl alcohol being even more preferred. The term "cetanol" as used herein means a mixture of alcohols composed mainly of cetyl alcohol and containing a higher alcohol such as stearyl alcohol or oleyl alcohol.

As the ester oil, preferred are monoester oils and one or two or more, as a mixture, of ester oils each having, in the molecule thereof, at least two ester bonds.

Examples of the monoester oil include monoester oils having in total 8 to 40 carbon atoms, preferably monoesters of a monohydric fatty acid having from 2 to 22, preferably from 8 to 20 carbon atoms and a monohydric or polyhydric alcohol having from 1 to 20 carbon atoms or the like. They may be linear or branched, and saturated or unsaturated. Preferred specific examples include isopropyl palmitate, isopropyl myristate, isononyl isononanoate, triisodecyl isononanoate, stearyl stearate, and diglyceryl monoisostearate.

Examples of the polyvalent ester oil having, in the molecule thereof, at least two ester bonds include polyvalent ester oils having in total 8 to 120 carbon atoms, preferably polyvalent esters composed of a mixture of one or two or more of mono- or polyhydric $C_{2-22}$ fatty acids and a mixture of one or two or more of mono- or polyhydric $C_{2-20}$ alcohols. They may be linear or branched, saturated or unsaturated, and may further contain an aromatic ring. More specifically, neopentyl glycol dicaprylate, diglyceryl diisostearate, and esters of dipentaerythritol with a mixture of fatty acids such as hydroxystearic acid, stearic acid and rosin.

Examples of the silicones include (a) dimethyl polysiloxane, (b) methylphenyl polysiloxane, (c) amino-modified silicones [aqueous silicone emulsions include "SM8704C" (commercially available from Dow Corning Toray Co., Ltd.) and "DC939" (commercially available from Dow Corning Toray Co., Ltd) or the like, (d) fatty-acid-modified polysiloxanes, (e) alcohol-modified silicones, (f) aliphatic alcohol-modified polysiloxanes, (g) polyether-modified silicones, (h) epoxy-modified silicones, (i) fluorine-modified silicones, (j) cyclic silicones, (k) alkyl-modified silicones, and (l) amino-modified siloxane-polyoxyalkylene block copolymers, which are described in JP-A-6-48916.

Two or more of these oily components may be used in combination. The content of it (them) in the hair treatment composition is preferably from 1 to 10% by weight, more preferably from 1.5 to 8% by weight, still more preferably from 2 to 5% by weight from the standpoint of giving finger combability and smoothness to the moisturized hair, moisturized feel after drying, and emulsion stability.

A weight ratio of the component (A) to the component (D) (oily component) [(A)/(D)] is preferably from 1/5 to 5/1, more preferably from 1/5 to 3/1, even more preferably from 1/4 to 2/1, still more preferably from 1/3 to 1 from the standpoints of suppressing transfer of an oily feel to hands and improving suppleness (lack of stiffness) of the hair and manageability of the hair.

A weight ratio of the component (A) to the component (C) (surfactant) [(A)/(C)] is preferably from 1/5 to 5/1, more preferably from 1/5 to 3/1, even more preferably from 1/3 to 3/1 from the standpoints of suppressing transfer of an oily feel to hands and improving suppleness (lack of stiffness) of the hair and manageability of the hair.

The hair treatment composition may contain a high molecular weight thickener. Examples of the high molecular weight thickener include hydroxyethyl cellulose, guar gum, xanthan gum, and polyacrylic acid polymers. The content of the high molecular weight thickener in the treatment composition is preferably from 0.01 to 20% by weight, more preferably from 0.05 to 15% by weight.

The hair treatment composition of the present invention may contain a protein hydrolysate typified by water soluble collagen and collagen derivatives which are known components to be incorporated in the hair treatment agent. It may also contain a chelating agent, a colorant, an antiseptic, a pH regulator, a viscosity regulator, a fragrance, a pearlescent agent, a humectant, or the like.

In addition to the above-described components, the hair treatment composition of the present invention may contain other components which are used ordinarily as raw materials for cosmetics. Examples of such an optional component include higher fatty acids, natural or synthetic polymers, ethers, protein derivatives, hydrolyzed proteins, amino acids, stabilizers, antioxidants, animal/vegetable extracts, crude drug extracts, vitamins, and UV absorbers.

As described above, the hair treatment composition of the present invention is used as hair treatment compositions such as permanent wave agents and hair dyes (including bleaching agents).

The hair treatment composition of the present invention may be provided in various forms such as liquid, emulsion, cream, gel, and mousse. Of these, an emulsified composition is more preferred.

When the hair treatment composition of the present invention is provided in the form of an emulsified composition, the number of carbon atoms in $R^1$ of the component A is preferably from 8 to 10 to cause the component (A) to function more as an oil component from the standpoint of improving the conditioning performance.

The hair treatment composition in the form of an emulsified composition may be prepared by heating a mixture of a surfactant and water, then adding the component (A) together with the oily component to the resulting mixture of a surfactant and water to form an emulsion, and followed by cooling the resulting emulsion and then adding the component (B) thereto; or heating a mixture of a surfactant and water, then adding an oily component while heating the resulting mixture, thereby preparing an emulsion, and followed by cooling the resulting emulsion and then adding the components (A) and (B) thereto. A suspended composition or clear composition may be obtained by mixing and stirring the component (A) and the component (B) to disperse or solubilize them.

The hair treatment composition of the present invention can be prepared, in addition to as an emulsified composition, as a suspended composition or clear composition in the conventional manner. The form thereof can be provided as a desired form such as lotion, cream, emulsion, gel, and aerosol foam.

EXAMPLES

The present invention will hereinafter be described more specifically by the following Examples, however the present invention is not limited thereto.

Preparation Example 1

An autoclave was charged with 1615.0 g (12.35 mol) of 1-octanol ("KALCOL 0898", commercially available from Kao Corporation) and 6.9 g (0.12 mol) of potassium hydroxide. After dehydration at 110° C. and 13.3 kPa, addition reaction was performed while pressing 1434 g (24.69 mol) of propylene oxide into the mixture at 0.3 MPa and 120° C.

After completion of the reaction, the reaction mixture was aged for 6 hours at the same reaction temperature, followed by cooling to 80° C.

To the reaction composition thus obtained was added 55 g of a synthetic adsorbent ("Kyowaad 600S", commercially available from Kyowa Chemical Industry Co., Ltd.) and the composition was treated with the adsorbent for 1 hour at 4.0 kPa. Then, the reaction mixture was filtered to remove the catalyst. The content of 1-octanol in the resulting filtrate was determined using gas chromatography, resulting in 9000 ppm.

From 1000 g of the filtrate, 1-octanol was distilled off under the conditions of 130° C. at 1.3 kPa. Further, steam treatment was performed by blowing 100 g of steam into the residue under the conditions of 145° C., 6.0 kPa, and 5 hours.

The 1-octanol content in the component (A) thus obtained (Alkylene glycol ether 1 shown in Table 1) was determined using gas chromatography.

Conditions of Gas Chromatography:
Gas chromatograph: "HP6890N", commercially available from Agilent Technologies
Column: "Ultra-Alloy-1", commercially available from Frontier Laboratories Ltd.
Temperature Conditions:
  Initial temperature: 100° C. (0 min)
  Heating rate: 10° C./min (up to 350° C.)
  Final temperature: 350° C. (20 min)
Sample amount: 1 μL
Condition of inlet: Split mode injection
  Temperature of inlet: 300° C.
Carrier gas: helium, flow rate: 60 mL/min
Detector: FID Distribution of the PO addition mole number in the component (A) was determined using gas chromatography before distillation and after distillation and steam treatment.
Distribution (Molar Ratio) of PO from 1 to 5 in the Alkylene Glycol Ether 1 Before Distillation
  The PO addition mole number 1: 35.6
  The PO addition mole number 2: 34.9
  The PO addition mole number 3: 18.7
  The PO addition mole number 4: 7.8
  The PO addition mole number 5: 3.0
Distribution (Molar Ratio) of PO from 1 to 5 in the Alkylene Glycol Ether 1 as the Component (A) after distillation and steam treatment
  The PO addition mole number 1: 24.6
  The PO addition mole number 2: 39.8
  The PO addition mole number 3: 22.4
  The PO addition mole number 4: 9.5
  The PO addition mole number 5: 3.7

Preparation Example 6

An autoclave was charged with 131.00 g (1.0 mol) of 1-octanol ("KALCOL 0898", commercially available from Kao Corporation) and 1.17 g (0.01 mol) of potassium hydroxide. After dehydration at 110° C. and 13.3 kPa, addition reaction was performed while pressing 151.01 g (2.6 mol) of propylene oxide into the mixture at 0.3 MPa and 120° C.

After completion of the reaction, the reaction mixture was aged for 6 hours at the same reaction temperature, followed by cooling to 80° C.

To the reaction composition thus obtained was added 55 g of a synthetic adsorbent ("Kyowaad 600S", commercially available from Kyowa Chemical Industry Co., Ltd.) and the composition was treated with the adsorbent for 1 hour at 4.0 kPa. Then, the reaction mixture was filtered to remove the catalyst. The content of 1-octanol in the resulting filtrate was determined using gas chromatography, resulting in 5000 ppm.

From 100 g of the filtrate, 1-octanol was distilled off under the conditions of 130° C. at 1.3 kPa. Further, steam treatment was performed by blowing 15 g of steam into the residue under the conditions of 145° C., 6.0 kPa, and 5 hours.

The 1-octanol content in the component (A) thus obtained (Alkylene glycol ether 6 shown in Table 1) was determined using gas chromatography.
Distribution (Molar Ratio) of PO from 1 to 5 in the Alkylene Glycol Ether 6 Before Distillation
  The PO addition mole number 1: 21.8
  The PO addition mole number 2: 32.0
  The PO addition mole number 3: 24.7
  The PO addition mole number 4: 14.2
  The PO addition mole number 5: 7.3
Distribution (Molar Ratio) of PO from 1 to 5 in the Alkylene Glycol Ether 6 as the Component (A) after distillation and steam treatment
  The PO addition mole number 1: 10.9
  The PO addition mole number 2: 34.9
  The PO addition mole number 3: 28.9
  The PO addition mole number 4: 16.7
  The PO addition mole number 5: 8.6

Preparation Examples 2 to 5 and 7 to 16

In a manner similar to that employed in Preparation Example 1, alkylene glycol ethers 2 to 5 and 7 to 16 shown in Tables 1 and 2 were obtained. After the alkylene glycol ethers 2 to 5, 7 to 10, 12, 14 to 16 were similarly treated with an adsorbent as in Preparation Example 1, they were purified using distillation and steam treatment while controlling the pressure reduction degree (pressure) or time to give the respective raw material alcohol contents shown in Tables 1 and 2. The alkylene glycol ethers 11 and 13 were treated with an adsorbent but not distilled. The raw material alcohol content in the resulting alkylene glycol ethers was determined using gas chromatography.

The average addition mole number n of PO and the average addition mole number m of EO, each in the alkylene glycols obtained in Tables 1 and 2, were determined using $^1$H-NMR.

TABLE 1

Preparation Example 1

Formula (1)

| | R[1]** | R[2] | n | m | Raw material alcohol content (ppm) |
|---|---|---|---|---|---|
| Alkylene glycol ether 1 | $C_8$ | H | 2.4 | 0 | 400 |
| Alkylene glycol ether 2 | $C_8$ | H | 1.6 | 0 | 1500 |
| Alkylene glycol ether 3 | $C_8/C_{10}$ (molar ratio: 1/1) | H | 3 | 0 | 900 |
| Alkylene glycol ether 4* | $C_8$ | H | 2 | 0.5 | 500 |
| Alkylene glycol ether 5 | 2-ethylhexyl | H | 3 | 0 | 400 |
| Alkylene glycol ether 6 | $C_8$ | H | 2.7 | 0 | 400 |
| Alkylene glycol ether 16 | $C_8$ | H | 5 | 0 | 400 |

*$(PO)_n/(EO)_m$ is arranged in blocks in the order of $(PO)_n$ and $(EO)_m$ relative to $R^1$.
**$C_8$: n-octyl, $C_{10}$: n-decyl

TABLE 2

Preparation Example 2

Formula (1)

| | R[1]** | R[2] | n | m | Raw material alcohol content (ppm) |
|---|---|---|---|---|---|
| Alkylene glycol ether 7 | $C_8$ | H | 6 | 0 | 400 |
| Alkylene glycol ether 8 | $C_8$ | H | 6 | 0 | 26000 |
| Alkylene glycol ether 9 | $C_8$ | H | 0 | 2 | 30000 |
| Alkylene glycol ether 10 | $C_8/C_{18}$ (molar ratio: 1/1) | H | 0 | 9 | 5000 |
| Alkylene glycol ether 11 | $C_8$ | H | 0 | 3 | 190000 |
| Alkylene glycol ether 12 | $C_{12}$ | H | 0 | 6 | 50000 |
| Alkylene glycol ether 13 | 2-ethylhexyl | H | 0 | 4 | 150000 |
| Alkylene glycol ether 14* | | | | | 2500 |
| Alkylene glycol ether 15 | $C_8$ | H | 2.7 | 0 | 12000 |

*$R-O-(C_2H_4O)_p-[(C_2H_4O)_q/(AO)_r]-H[(C_2H_4O)_q/(AO)_r]$ is arranged at random. R = isodecyl, p = 4, q = 1.5, AO = PO, r = 1.5
**$C_8$: n-octyl, $C_{10}$: n-decyl, $C_{12}$: n-dodecyl, $C_{18}$: n-octadecyl Examples 1 to 8 and Comparative Examples 1 to 10

Two-part hair dyes (first-part and second-part agents) having the compositions as shown in Tables 3 and 4 were prepared, respectively, by using the below-described processes and they were evaluated for spreadability upon application of the dyes to the hair (tress) and hair feel (manageability of the hair and suppleness (lack of stiffness) of the hair) upon finishing the treatment thereof.

First-part agent: Stir a mixture of Components 2 to 10 and an adequate amount of water. After heating to 80° C., add a mixture obtained in advance by mixing Component 1 with Components 11 to 14 and heating to 80° C. to the above-mentioned mixture to cause emulsification. Cool the emulsion thus obtained to 40° C., add Components 15 and 16 and a remaining portion of water, and mix the resulting mixture uniformly.

Second-part agent: Stir a mixture of Components 2 to 6 with an adequate amount of water. After heating to 80° C., add a mixture obtained in advance by mixing Component 1 with Components 7 and 8 and heating to 80° C. to the above-mentioned mixture to cause emulsification. After cooling the resulting emulsion to 40° C., add Component 9 thereto and mix them uniformly.

The pH (20° C.) of the first-part agents in Table 3 was 9.8 and the pH (20° C.) of the second-part agent in Table 4 was 3.2.

The unit % in Tables 3 and 4 means % by weight.
[Evaluation Test of Hair Treatment Composition]
The evaluation method and evaluation criteria will next be described.

Organoleptic evaluation on the spreadability upon application of the composition to the hair and the manageability and suppleness (lack of stiffness) of the hair upon finishing of the treatment was performed by a panel of experts while using a test tress. Described specifically, about 20-cm long black straight hair of an adult woman not subjected to chemical treatments was used as a specimen. It was washed by dipping it in a sodium lauryl sulfate solution of from 40 to 50° C. for 10 minutes, washed with running water, and then air dried. About 4 g of the resulting hair specimen was arranged to give a uniform thickness and a width of 3 cm. One end of the hair was fixed to a plastic plate of 3 cm wide with an adhesive to give a hair length of 15 cm. It was provided as a test tress. The test tress thus prepared was used for the evaluation.
Evaluator and Tress:
A panel of five experts touched the tress and organoleptically evaluated the hair feel based on the following criteria.
Operation: Wet the tress sufficiently with warm water of from 35 to 40° C. and then shampoo it with a plain shampoo having the below-described composition. After rinsing it sufficiently with warm water, towel dry the excess water of the tress and dry it with a drier sufficiently. Apply 4 g of a hair cosmetic composition (a mixture of equal amounts of the first-part agent and the second-part agent) (pH after mixture is 9.5 (20° C.)) to the tress. After evaluating spreadability upon application, rinse it with warm water, towel dry the excess water, and run a comb through the tress. Then, dry it with a warm air from a drier, run a comb through the tress as a finish treatment, and evaluate each item upon finishing.

| Plain shampoo | (% by weight) |
|---|---|
| Emal E-27C | 42 |
| (commercially available from Kao Corporation) | |
| [Sodium polyoxyethylene lauryl ether sulfate: purity 27 wt %] | |
| Aminon C-11S | 3 |
| (commercially available from Kao Corporation) | |
| [Cocamide N-methylethanolamide] | |
| Citric acid | 0.2 |
| Methylparaben | 0.3 |
| Purified water | Balance |
| Total | 100 |

Evaluation of Spreadability of Hair Dye on Hair (Tress) Upon Application to the Hair
Evaluation Criteria:
3: Good spreadability upon application to hair
2: Little inferior in spreadability upon application to hair
1: Poor spreadability upon application to hair
Each score was determined by averaging the evaluation results of five experts.
Manageability of Hair (Visually Evaluated)
Evaluation Criteria:
3: Good manageability without flyaway hair
2: Inferior in manageability with some flyaway hair
1: Poor manageability with much flyaway hair
Each score was determined by averaging the evaluation results of five experts.
Suppleness (Lack of Stiffness) of Hair (Evaluated Visually and by Touching the Hair with Hands).
Evaluation Criteria:
3: Moisturized and not stiff to the touch
2: Slightly moisturized and slightly stiff to the touch
1: Dry and stiff to the touch Each score was determined by averaging the evaluation results of five experts.

TABLE 3

Formulation example of first part agent of two-part hair dye

| Components | Raw materials | 1 wet % | 2 wet % | 3 wet % | 4 wet % | 5 wet % | 6 wet % | 7 wet % | 8 wet % | 9 wet % |
|---|---|---|---|---|---|---|---|---|---|---|
| 1 | Alkylene glycol ether 1 | 3.0 | | | | | | | | |
|  | Alkylene glycol ether 2 | | 3.0 | | | | | | | |
|  | Alkylene glycol ether 3 | | | 3.0 | | | | | | |
|  | Alkylene glycol ether 4 | | | | 3.0 | | | | | |
|  | Alkylene glycol ether 5 | | | | | 3.0 | | | | |
|  | Alkylene glycol ether 6 | | | | | | 3.0 | | | |
|  | Alkylene glycol ether 7 | | | | | | | 3.0 | | |
|  | Alkylene glycol ether 8 | | | | | | | | 3.0 | |
|  | Alkylene glycol ether 9 | | | | | | | | | 3.0 |
|  | Alkylene glycol ether 10 | | | | | | | | | |
|  | Alkylene glycol ether 11 | | | | | | | | | |
|  | Alkylene glycol ether 12 | | | | | | | | | |
|  | Alkylene glycol ether 13 | | | | | | | | | |
|  | Alkylene glycol ether 14 | | | | | | | | | |
|  | Alkylene glycol ether 15 | | | | | | | | | |
|  | Alkylene glycol ether 16 | | | | | | | | | |
| 2 | Toluene-2,5-diamine | 1 | 1 | 1 | 1 | 1 | 1 | 1 | 1 | 1 |
| 3 | 5-Amino-ortho-cresol | 0.02 | 0.02 | 0.02 | 0.02 | 0.02 | 0.02 | 0.02 | 0.02 | 0.02 |
| 4 | Meta-aminophenol | 0.12 | 0.12 | 0.12 | 0.12 | 0.12 | 0.12 | 0.12 | 0.12 | 0.12 |
| 5 | Para-aminophenol | 0.58 | 0.58 | 0.58 | 0.58 | 0.58 | 0.58 | 0.58 | 0.58 | 0.58 |
| 6 | Resorcin | 0.47 | 0.47 | 0.47 | 0.47 | 0.47 | 0.47 | 0.47 | 0.47 | 0.47 |
| 7 | EDTA-4Na | 0.2 | 0.2 | 0.2 | 0.2 | 0.2 | 0.2 | 0.2 | 0.2 | 0.2 |
| 8 | Anhydrous sodium sulfite | 1.0 | 1.0 | 1.0 | 1.0 | 1.0 | 1.0 | 1.0 | 1.0 | 1.0 |
| 9 | Ascorbic acid | 0.5 | 0.5 | 0.5 | 0.5 | 0.5 | 0.5 | 0.5 | 0.5 | 0.5 |
| 10 | Sodium lauryl sulfate | 1.7 | 1.7 | 1.7 | 1.7 | 1.7 | 1.7 | 1.7 | 1.7 | 1.7 |
| 11 | Stearyl alcohol | 6.0 | 6.0 | 6.0 | 6.0 | 6.0 | 6.0 | 6.0 | 6.0 | 6.0 |
| 12 | Cocamide MEA | 4.6 | 4.6 | 4.6 | 4.6 | 4.6 | 4.6 | 4.6 | 4.6 | 4.6 |
| 13 | Propylene glycol | 1.0 | 1.0 | 1.0 | 1.0 | 1.0 | 1.0 | 1.0 | 1.0 | 1.0 |
| 14 | D-pantothenyl alcohol | 0.25 | 0.25 | 0.25 | 0.25 | 0.25 | 0.25 | 0.25 | 0.25 | 0.25 |
| 15 | Aqueous ammonia (28 wt %) | 8.2 | 8.2 | 8.2 | 8.2 | 8.2 | 8.2 | 8.2 | 8.2 | 8.2 |
| 16 | Ammonium chloride | 0.5 | 0.5 | 0.5 | 0.5 | 0.5 | 0.5 | 0.5 | 0.5 | 0.5 |
|  | Purified water | Balance | Balance | Balance | Balance | Balance | Balance | Balance | Balance | Balance |

| Components | Raw materials | 10 wet % | 11 wet % | 12 wet % | 13 wet % | 14 wet % | 15 wet % | 16 wet % | 19 wet % |
|---|---|---|---|---|---|---|---|---|---|
| 1 | Alkylene glycol ether 1 | | | | | | | | |
|  | Alkylene glycol ether 2 | | | | | | | | |
|  | Alkylene glycol ether 3 | | | | | | | | |
|  | Alkylene glycol ether 4 | | | | | | | | |
|  | Alkylene glycol ether 5 | | | | | | | | |
|  | Alkylene glycol ether 6 | | | | | | | | |
|  | Alkylene glycol ether 7 | | | | | | | | |
|  | Alkylene glycol ether 8 | | | | | | | | |
|  | Alkylene glycol ether 9 | 3.0 | | | | | | | |
|  | Alkylene glycol ether 10 | | 3.0 | | | | | | |
|  | Alkylene glycol ether 11 | | | 3.0 | | | | | |
|  | Alkylene glycol ether 12 | | | | 3.0 | | | | |
|  | Alkylene glycol ether 13 | | | | | 3.0 | | | |
|  | Alkylene glycol ether 14 | | | | | | 3.0 | | |
|  | Alkylene glycol ether 15 | | | | | | | 3.0 | |
|  | Alkylene glycol ether 16 | | | | | | | | 3.0 |
| 2 | Toluene-2,5-diamine | 1 | 1 | 1 | 1 | 1 | 1 | 1 | 1 |
| 3 | 5-Amino-ortho-cresol | 0.02 | 0.02 | 0.02 | 0.02 | 0.02 | 0.02 | 0.02 | 0.02 |
| 4 | Meta-aminophenol | 0.12 | 0.12 | 0.12 | 0.12 | 0.12 | 0.12 | 0.12 | 0.12 |
| 5 | Para-aminophenol | 0.58 | 0.58 | 0.58 | 0.58 | 0.58 | 0.58 | 0.58 | 0.58 |
| 6 | Resorcin | 0.47 | 0.47 | 0.47 | 0.47 | 0.47 | 0.47 | 0.47 | 0.47 |
| 7 | EDTA-4Na | 0.2 | 0.2 | 0.2 | 0.2 | 0.2 | 0.2 | 0.2 | 0.2 |
| 8 | Anhydrous sodium sulfite | 1.0 | 1.0 | 1.0 | 1.0 | 1.0 | 1.0 | 1.0 | 1.0 |
| 9 | Ascorbic acid | 0.5 | 0.5 | 0.5 | 0.5 | 0.5 | 0.5 | 0.5 | 0.5 |
| 10 | Sodium lauryl sulfate | 1.7 | 1.7 | 1.7 | 1.7 | 1.7 | 1.7 | 1.7 | 1.7 |
| 11 | Stearyl alcohol | 6.0 | 6.0 | 6.0 | 6.0 | 6.0 | 6.0 | 6.0 | 6.0 |
| 12 | Cocamide MEA | 4.6 | 4.6 | 4.6 | 4.6 | 4.6 | 4.6 | 4.6 | 4.6 |
| 13 | Propylene glycol | 1.0 | 1.0 | 1.0 | 1.0 | 1.0 | 1.0 | 1.0 | 1.0 |
| 14 | D-pantothenyl alcohol | 0.25 | 0.25 | 0.25 | 0.25 | 0.25 | 0.25 | 0.25 | 0.25 |
| 15 | Aqueous ammonia (28 wt %) | 8.2 | 8.2 | 8.2 | 8.2 | 8.2 | 8.2 | 8.2 | 8.2 |
| 16 | Ammonium chloride | 0.5 | 0.5 | 0.5 | 0.5 | 0.5 | 0.5 | 0.5 | 0.5 |
|  | Purified water | Balance | Balance | Balance | Balance | Balance | Balance | Balance | Balance |

TABLE 4

Formulation example of second-part agent of two-part hair dye

| Components | Raw materials | 17 wet % | 18 wet % |
|---|---|---|---|
| 1 | Alkylene glycol ether 3 |  | 0.5 |
| 2 | EDTA-4Na | 0.05 | 0.05 |
| 3 | Salicylic acid | 0.01 | 0.01 |
| 4 | Disodium hydrogen phosphate | 0.11 | 0.11 |
| 5 | Phosphoric acid | 0.4 | 0.4 |
| 6 | Sodium lauryl sulfate | 0.19 | 0.19 |
| 7 | Stearyl alcohol | 1.71 | 1.71 |
| 8 | D-pantothenyl alcohol | 0.25 | 0.25 |
| 9 | Aqueous hydrogen peroxide (35 wt %) | 6.0 | 6.0 |
|  | Purified water | Balance | Balance | dyeing properties were measured by using a test tress described below and they were organoleptically evaluated by a panel of experts.

Evaluator and Tress:

One expert treated tress with each of the hair dye compositions and evaluated their spreadability upon application to the hair. Then, these five experts including the expert who had treated the tress organoleptically evaluated the dyed tresses for the above-described hair feel based on the criteria described below.

Each tress was prepared by using a commercially available tress for confirming hair dyeing properties (bleached hair, weight of tress: about 1 g, straight hair) as a specimen, dipping and washing it in a sodium lauryl sulfate solution of from 40 to 50° C. for 10 minutes, washing it with running water, and then air drying it. Three tresses were prepared per sample.

TABLE 5

Two-part hair dye: Combination of first-part and second-part agents and evaluation results of performance

|  |  | Examples | | | | | | | | Comparative Examples | | | | | | | | | |
|---|---|---|---|---|---|---|---|---|---|---|---|---|---|---|---|---|---|---|---|
|  |  | 1 | 2 | 3 | 4 | 5 | 6 | 7 | 8 | 1 | 2 | 3 | 4 | 5 | 6 | 7 | 8 | 9 | 10 |
| Formulation example No. of first-part agent | | 1 | 2 | 3 | 4 | 5 | 6 | 7 | 19 | 8 | 9 | 10 | 11 | 12 | 13 | 14 | 15 | 7 | 16 |
| Formulation example No. of second-part agent | | 17 | 17 | 17 | 17 | 17 | 17 | 18 | 17 | 17 | 17 | 17 | 17 | 17 | 17 | 17 | 17 | 17 | 17 |
| Raw material alcohol (ppm) in the formulation of first-part agent | | 12 | 45 | 27 | 15 | 12 | 12 | 0 | 12 | 12 | 780 | 900 | 150 | 5700 | 1500 | 4500 | 75 | 0 | 0 |
| Raw material alcohol (ppm) in the formulation of second-part agent | | 0 | 0 | 0 | 0 | 0 | 0 | 4.5 | 0 | 0 | 0 | 0 | 0 | 0 | 0 | 0 | 0 | 0 | 0 |
| Upon application to hair | spreadability | 3 | 3 | 3 | 2.6 | 2.4 | 3 | 2.4 | 2.6 | 2 | 2 | 1.4 | 1.4 | 1.4 | 1 | 1 | 1.4 | 1 | 2 |
| Upon finishing | Lack of stiffness | 3 | 3 | 3 | 2.8 | 3 | 3 | 2.4 | 2.4 | 2.4 | 2 | 1.6 | 1.6 | 1.4 | 1 | 1 | 1 | 1 | 2.2 |
|  | Manageability | 3 | 3 | 3 | 3 | 2.8 | 3 | 2.8 | 2.8 | 2 | 2 | 1 | 1 | 1 | 1 | 1 | 1 | 1 | 1.8 |

It has been understood from Table 5 that the hair treatment compositions of the present invention are excellent in spreadability upon application to the hair and capable of imparting good suppleness (lack of stiffness) and manageability to the hair upon finishing, without damaging their hair dying properties. Any of the compositions had good hair dyeing properties.

Examples 9 to 12 and Comparative Example 11

One-part hair dye compositions having the compositions as shown in Table 6 were prepared using the below-described process and they were evaluated for spreadability upon application of the compositions to the hair (tress) and hair feel (manageability and suppleness (lack of stiffness) of the hair) upon finishing the treatment thereof and hair dyeing properties.

The one-part hair dyes were obtained by mixing and then stirring the components shown in Table 6. The aqueous solution of sodium hydroxide (48 wt %) was added to them so as to be a pH (20° C.) of 3. The unit % in Table 6 means % by weight.

[Evaluation Test of Hair Treatment Composition]

The evaluation method and evaluation criteria are shown below.

Spreadability upon application of the hair dye compositions to the hair and manageability and suppleness (lack of stiffness) of the hair upon finishing the treatment and hair Operation:

Prepare three tresses, each weighing 1 g, and apply 1 g per tress of the hair dye composition to each of the tresses by using a brush. Evaluate the spreadability of the hair dye composition. Allow the tress to stand for 15 minutes under the environment of 30° C., wash with warm water to remove excess hair dye composition, shampoo with 0.5 g per tress of a plain shampoo for 15 seconds, and rinse with warm water for 30 seconds. Towel dry the tress, run a comb through it, and dry it with the warm air from a drier. As a finishing operation, run a comb through the tress. Evaluate three tresses collectively for each item upon finishing. The plain shampoo used here is similar to that used for evaluation in Example 1.

Evaluation of Spreadability of Hair Dye on Hair (Tress) Upon Application to Hair Evaluation Criteria:
3: Good spreadability upon application to hair
2: Little inferior in spreadability upon application to hair
1: Poor spreadability upon application to hair Each score was determined from the evaluation results of an expert.

Manageability of Hair (Visually Evaluated)
Evaluation Criteria:
3: Good manageability without flyaway hair
2: Inferior in manageability with some flyaway hair
1: Poor manageability with much flyaway hair Each score was determined by averaging the evaluation results of the five experts.

Suppleness (Lack of Stiffness) of Hair (Evaluated Visually and by Touching the Hair with Hands).
Evaluation Criteria:
3: Moisturized and not stiff to the touch
2: Slightly moisturized and slightly stiff to the touch
1: Dry and stiff to the touch
Each score was determined by averaging the evaluation results of the five experts.
Hair Dyeing Properties (Evaluated Visually)
Evaluation Criteria:
3: The tresses are colored firmly without dyeing unevenness.
2: The tresses seem white, though having no dyeing unevenness.
1: The tresses entirely seem white with dyeing unevenness.
Each score was determined by averaging the evaluation results of the five experts.

TABLE 6

One-part hair dye: formulation and evaluation results of performance

| Raw materials | | Comparative Example 11 wet % | Examples 9 wet % | 10 wet % | 11 wet % | 12 wet % |
|---|---|---|---|---|---|---|
| Alkylene glycol ether 1 | | 0.0 | 1.0 | 2.5 | 5.0 | 10.0 |
| Black No. 401 | | 0.2 | 0.2 | 0.2 | 0.2 | 0.2 |
| L-Lactic acid | | 4.5 | 4.5 | 4.5 | 4.5 | 4.5 |
| Ethanol | | 9.0 | 9.0 | 9.0 | 9.0 | 9.0 |
| Benzyl alcohol | | 5.0 | 5.0 | 5.0 | 5.0 | 5.0 |
| Hydroxypropyl xanthan gum 1) | | 1.5 | 1.5 | 1.5 | 1.5 | 1.5 |
| Aqueous solution of sodium hydroxide (48 wt %) | | q.s.* | q.s.* | q.s.* | q.s.* | q.s.* |
| Purified water | | Balance | Balance | Balance | Balance | Balance |
| Raw material alcohol in formulation (ppm) | | 0 | 1 | 10 | 20 | 40 |
| Upon application to hair | Spreadability | 2 | 3 | 3 | 3 | 3 |
| Upon finishing | Lack of stiffness | 2.2 | 3 | 3 | 3 | 3 |
| | Manageability | 2 | 2.6 | 3 | 3 | 3 |
| | Dyeing properties | 3 | 3 | 3 | 2.6 | 1.4 |

1) "Rhaball gum EX" commercially available from Dainippon Sumitomo Pharma Co., Ltd.
*It is added so as to be a pH (20° C.) of 3.

It has been understood from Table 6 that the hair treatment compositions of the present invention are excellent in spreadability upon application to the hair and capable of imparting good suppleness (lack of stiffness) and manageability to the hair upon finishing, without damaging their hair dyeing properties.

Example 13

One-Part Hair Dye

The components shown in Table 7 were mixed and then stirred to obtain a one-part hair dye. The aqueous solution of sodium hydroxide (48 wt %) was added to them so as to be a pH (20° C.) of 3. The unit % in Table 7 means % by weight.

TABLE 7

Example 13
One-part hair dye composition

| Raw materials | 13 wet % |
|---|---|
| Alkylene glycol ether 1 | 6.00 |
| Orange No. 205 | 0.48 |
| Black No. 401 | 0.28 |
| Violet No. 401 | 0.03 |
| Red No. 227 | 0.04 |
| Aqueous solution of glycolic acid (71 wt %) | 4.00 |
| Ethanol | 7.00 |
| Benzyloxyethanol | 5.00 |
| Glycerin | 1.00 |
| ($C_{12-14}$) Pareth-9 | 0.24 |
| PEG-9 Dimethicone[1] | 0.80 |
| PEG-11 Methyl ether dimethicone[2] | 0.80 |
| Hydroxypropyl xanthan gum[3] | 1.40 |
| Aqueous solution of sodium hydroxide (48 wt %) | q.s.* |
| Purified water | Balance |

Raw material alcohol 24 ppm
[1] "KF-6005" commercially available from Shin-etsu Chemical Co., Ltd.
[2] "KF-6011" commercially available from Shin-etsu Chemical Co., Ltd.
[3] "Rhaball gum EX" commercially available from Dainippon Sumitomo Pharma Co., Ltd.
*It is added so as to be a pH (20° C.) of 3.

The one-part hair dye thus obtained showed good spreadability upon application to the hair (tress), had good hair dyeing properties, and imparted good suppleness (lack of stiffness) and manageability to the hair upon finishing after rinsing with warm water.

Example 14

Decolorizing Agent

Stir a mixture of PEG hydrogenated castor oil, Polysorbate-40, an organic acid, a salt of an organic acid, and an adequate amount of water. After heating the resulting mixture to 80° C., add a mixture obtained in advance by mixing alkylene glycol ether, cetyl alcohol, and Ceteth-40 and then heating to 80° C. to the above-mentioned mixture to cause emulsification. Cool the emulsion to 40° C., add aqueous hydrogen peroxide and a remaining portion of water to the emulsion, and mix uniformly. The resulting mixture had a pH (20° C.) of 2.5. The unit % in Table 8 means % by weight.

TABLE 8

Example 14
One-part decolorizing agent composition

| Raw materials | 14 wet % |
|---|---|
| Alkylene glycol ether 2 | 3.00 |
| Aqueous hydrogen peroxide (35 wt %) | 15.00 |
| Cetyl alcohol | 10.00 |
| Ceteth-40 | 3.00 |
| PEG hydrogenated castor oil | 0.50 |
| Polysorbate 40 | 0.50 |
| Dipropylene glycol | 2.00 |
| EDTA-4Na | 0.05 |
| Salicylic acid | 0.01 |
| Disodium hydrogen phosphate | 0.11 |
| Phosphoric acid | 0.40 |
| Purified water | Balance |

Raw material alcohol 45 ppm

The one-part hair decolorizing agent thus obtained showed good spreadability upon application to the hair (tress), having good decolorizing properties, and imparted good suppleness (lack of stiffness) and manageability to the hair upon finishing after rinsing with warm water.

Examples 15 to 16

Permanent Wave Agent

First-part agent: Mix the components such as alkylene glycol ether and L-cysteine and stir the resulting mixture. Finally, add ammonium thioglycolate, ammonium dithioglycolate, monoethanolamine, aqueous ammonia, and the like and mix the resulting mixture uniformly.

Second-part agent: Mix the components and then stir the resulting mixture.

The first-part agent and the second-part agent of the permanent wave agent were thus prepared. The aqueous solution of ammonia (28 wt %) or monoethanolamine was added to the first part agent so as to be a pH (20° C.) of 9.0. The second part agent had a pH (20° C.) of 6.1. The unit % in Tables 9 and 10 means % by weight.

TABLE 9

Example 15
Permanent wave agent composition

First-part agent

| Raw materials | 15-A wet % |
|---|---|
| Alkylene glycol ether 4 | 10.00 |
| Ammonium thioglycolate (50 wt %) | 12.00 |
| Ammonium hydrogen carbonate | 2.50 |
| Ethanol | 5.00 |
| Propylene glycol | 5.00 |
| EDTA-2Na | 0.50 |

TABLE 9-continued

Example 15
Permanent wave agent composition

| Ceteth-20 | 1.00 |
|---|---|
| Ammonia (28 wt %) | q.s.* |
| Purified water | Balance |

Raw material alcohol 50 ppm
*It is added so as to be a pH (20° C.) of 9.0.

Second-part agent

| Raw materials | 15-B wet % |
|---|---|
| Sodium bromate | 7.50 |
| Propylene glycol | 5.00 |
| Ceteth-20 | 0.75 |
| Ceteth-2 | 0.25 |
| Amodimethicone 1) | 0.50 |
| Keratin hydrolysate 2) | 0.50 |
| Purified water | Balance |

1) "SM8904" Cosmetic Emulsion — commecially available from Dow Corning Toray Co., Ltd.
2) "Promois WK-H" — commecially available from Seiwa Kasei Co., Ltd.

TABLE 10

Example 16
Permanent wave agent composition

First-part agent

| Raw materials | 16-A wet % |
|---|---|
| Alkylene glycol ether 6 | 2.00 |
| Ammonium thioglycolate (50 wt %) | 1.50 |
| L-Cysteine | 4.50 |
| Ammonium dithioglycolate | 0.50 |
| Ethanol | 5.00 |
| Propylene glycol | 8.00 |
| EDTA-2Na | 0.50 |
| Ceteth-20 | 1 |
| Monoethanolamine | q.s.* |
| Purified water | Balance |

Raw material alcohol: 8 ppm
*It is added so as to be a pH (20° C.) of 9.0.

Second-part agent

| Raw materials | 16-B wet % |
|---|---|
| Alkylene glycol ether 6 | 5.00 |
| Sodium bromate | 8.00 |
| Propylene glycol | 8.00 |
| Ethanol | 3.00 |
| Ceteth-20 | 0.75 |
| Ceteth-2 | 0.25 |
| Amodimethicone1) | 0.50 |
| Keratin hydrolysate2) | 0.50 |
| Purified water | Balance |

Raw material alcohol: 20 ppm
1) "SM8904" Cosmetic Emulsion — commecially available from Dow Corning Toray Co., Ltd.
2) "Promois WK-H" — Commecially available from Seiwa Kasei Co., Ltd.

Both the first-part agent and the second-part agent of the permanent wave agent showed good spreadability upon application to the hair (tress), had good perming properties, and imparted good suppleness (lack of stiffness) and manageability to the hair upon finishing after rising with warm water.

Example 17

Hair Relaxer

First-part agent: The first-part agent was obtained by mixing an alkylene glycol ether, β-naphthalenesulfonic acid, and a solvent, stirring the resulting mixture, finally adding ammonium thioglycolate, ammonium hydrogen carbonate, and monoethanolamine, and mix the resulting mixture uniformly.

Second-part agent: The second-part agent was obtained by mixing an alkylene glycol ether, β-naphthalenesulfonic acid and a solvent, stirring the resulting mixture, finally adding aqueous hydrogen peroxide and sodium hydroxide, and mix the resulting mixture uniformly.

The first-part agent and the second-part agent of a hair relaxer were thus obtained. Monoethanolamine was added to the first-part agent so as to be a pH (20° C.) of 9.0, and the aqueous solution of sodium hydroxide (48 wt %) was added to the second-part agent so as to be a pH (20° C.) of 3.5. The unit % in Table 11 means % by weight.

TABLE 11

Example 17
Hair relaxer composition

First-part agent

| Raw materials | 17-A wet % |
|---|---|
| Alkylene glycol ether 5 | 5.00 |
| Ammonium thioglycolate (50 wt %) | 13.00 |
| Ammonium hydrogen carbonate | 2.00 |
| β-Naphthalenesulfonic acid | 5.00 |
| 2-Benzyloxyethanol | 3.50 |
| Ethanol | 7.00 |
| Propylene glycol | 5.00 |
| EDTA-2Na | 0.50 |
| Monoethanolamine | q.s.* |
| Purified water | Balance |

Raw material alcohol: 20 ppm
*It is added so as to be a pH (20° C.) of 9.0.

Second-part agent

| Raw materials | 17-B wet % |
|---|---|
| Alkylene glycol ether 6 | 1.00 |
| Aqueous hydrogen peroxide (35 wt %) | 5.00 |
| Lactic acid | 4.50 |
| β-Naphthalenesulfonic acid | 1.50 |
| 2-Benzyloxyethanol | 3.50 |
| Ethanol | 10.00 |
| Ceteth-20 | 1.00 |
| Aqueous solution of Sodium hydroxide (48 wt %) | q.s.* |
| Purified water | Balance |

Raw material alcohol: 4 ppm
*It is added so as to be a pH (20° C.) of 3.5.

A tress for evaluation of the resulting heat relaxer was prepared in the following manner. Hair provided by a Japanese adult woman having frizzy hair, not subjected to chemical treatments, and 12 cm long and weighing 10 g was used as a specimen. The hair was dipped in a solution of sodium lauryl sulfate of from 40 to 50° C. for 10 minutes, washed in the solution, washed with running water, and then air-dried. A test tress was prepared by arranging about 2.5 g of the hair specimen to a width of 2 cm to give a uniform thickness and fixing one end of it to a plastic plate of 2 cm wide with an adhesive so that the length of the hair would be 10 cm. The test tress thus prepared was provided for evaluation.

Both the first-part agent and the second-part agent of the heat relaxer thus obtained showed good spreadability upon application to the hair (tress: prepared using hair having frizzy hair in a large proportion). The hair relaxer imparted good suppleness (lack of stiffness) and manageability to the hair upon finishing after treating with the second agent and then rinsing with warm water and also showed good hair relaxing power (hair straightening property).

The invention claimed is:

1. A hair treatment composition for imparting good manageability and excellent feeling to the touch to the hair upon finishing of permanent waving or hair dyeing treatment, comprising the following components (A) and (B):

(A) a compound represented by the following formula (1):

$$R^1O-(PO)_n(EO)_m-R^2 \quad (1),$$

wherein $R^1$ represents a linear or branched $C_{8-12}$ alkyl or alkenyl group, PO represents a propyleneoxy group, EO represents an ethyleneoxy group, n represents an average addition mole number and is from 1.5 to 5.0, m represents an average addition mole number and is from 0 to 1.0, and $R^2$ represents a hydrogen atom or a methyl group, and (B) at least one member selected from the group consisting of keratin, a reducing agent, an oxidizing agent, an alkaline agent, and a dye for a hair dye.

2. The hair treatment composition according to claim 1, wherein the component (A) is a compound represented by the following formula (1):

$$R^1O-(PO)_n(EO)_m-R^2 \quad (1),$$

wherein $R^1$ represents a linear or branched $C_{8-12}$ alkyl or alkenyl group, PO represents a propyleneoxy group, EO represents an ethyleneoxy group, n represents an average addition mole number and is from 1.5 to 3.0, m represents an average addition mole number and is from 0 to 1.0, and $R^2$ represents a hydrogen atom or a methyl group.

3. The hair treatment composition according to claim 1, wherein the component (A) is a compound obtained by reacting a raw material alcohol represented by the formula $R^1OH$, wherein $R^1$ represents a linear or branched $C_{8-12}$ alkyl or alkenyl group, with propylene oxide or propylene oxide and ethylene oxide and then distilling off the raw material alcohol.

4. The hair treatment composition according to claim 3, wherein a content of the raw material alcohol in the component (A) is 3000 ppm or less.

5. The hair treatment composition according to claim 1, wherein a content of the component (A) is from 0.1 to 10% by weight.

6. The hair treatment composition according to claim 1, wherein a total proportion of compounds having 2 and 3 moles of a PO addition mole number based on compounds having 1 to 5 moles of a PO addition mole number present in the component (A) is from 58 to 80 mol%.

7. A method of preparing of a permanent wave agent or a hair dye composition, comprising adding, to a hair composition comprising at least one of a permanent wave agent and a hair dye, the following component (A) and component (B):

(A) a compound represented by the following formula (1):

$$R^1O-(PO)_n(EO)_m-R^2 \quad (1),$$

wherein $R^1$ represents a linear or branched $C_{8-12}$ alkyl or alkenyl group, PO represents a propyleneoxy group, EO represents an ethyleneoxy group, n represents an average addition mole number and is from 1.5 to 5.0, m represents an average addition mole number and is from 0 to 1.0, and $R^2$ represents a hydrogen atom or a methyl group; and (B) at least one member selected from the group consisting of keratin, a reducing agent, an oxidizing agent, an alkaline agent, and a dye for hair dye, wherein the hair composition is for imparting good manageability and excellent feeling to the touch to the hair upon finishing of permanent waving or hair dyeing treatment.

8. The method according to claim 7, wherein the component (A) is a compound represented by the following formula (1):

$$R^1O-(PO)_n(EO)_m-R^2 \quad (1),$$

wherein $R^1$ represents a linear or branched $C_{8-12}$ alkyl or alkenyl group, PO represents a propyleneoxy group, EO represents an ethyleneoxy group, n represents an average addition mole number and is from 1.5 to 3.0, m represents an average addition mole number and is from 0 to 1.0, and $R^2$ represents a hydrogen atom or a methyl group.

9. The method according to claim 7, wherein the component (A) is a compound obtained by reacting a raw material alcohol represented by the formula $R^1OH$, wherein $R^1$ represents a linear or branched $C_{8-12}$ alkyl or alkenyl group, with propylene oxide or propylene oxide and ethylene oxide and then distilling off the raw material alcohol.

10. The method according to claim 9, wherein a content of the raw material alcohol in the component (A) is 3000 ppm or less.

11. The method according to claim 7, wherein a content of the component (A) is from 0.1 to 10% by weight.

12. The method according to claim 7, wherein a total proportion of compounds having 2 and 3 moles of a PO addition mole number based on compounds having 1 to 5 moles of a PO addition mole number present in the component (A) is from 58 to 80 mol%.

13. A method of treating hair, comprising applying the hair treatment composite of claim 1 combined with at least one of a permanent wave agent and a hair dye to the hair.

14. The hair treatment composition according to claim 2, wherein the component (A) is a compound obtained by reacting a raw material alcohol represented by the formula $R^1OH$, wherein $R^1$ represents a linear or branched $C_{8-12}$ alkyl or alkenyl group, with propylene oxide or propylene oxide and ethylene oxide and then distilling off the raw material alcohol.

15. The hair treatment composition according to claim 14, wherein a content of the raw material alcohol in the component (A) is 3000 ppm or less.

16. The method according to claim 8, wherein the component (A) is a compound obtained by reacting a raw material alcohol represented by the formula $R^1OH$, wherein $R^1$ represents a linear or branched $C_{8-12}$ alkyl or alkenyl group, with propylene oxide or propylene oxide and ethylene oxide and then distilling off the raw material alcohol.

17. The method according to claim 16, wherein a content of the raw material alcohol is 3000 ppm or less.

18. The method according to claim 7, wherein $R^1$ represents a linear or branched $C_{8-10}$ alkyl or alkenyl group.

19. The method according to claim 7, wherein m represents an average addition mole number and is from 0 to 0.5.

20. The method according to claim 7, wherein a weight ratio of component (A) to component (B), (A)/(B), is from 1/10 to 10/1.

21. The method according to claim 7, wherein said keratin comprises at least one member selected from the group consisting of thioglycolic acid, a thioglycolic acid ester, thiolactic acid, a thiolactic acid ester, cysteine, a N-acylcysteine, a compounds represented by formula (2), a compound represented by the formula (3), and a salt thereof:

$$R^3OCH_2CH(OH)CH_2SH \quad (2)$$

wherein $R^3$ represents a hydrogen atom, a lower alkyl group, or a lower alkoxy lower alkyl group; and $$H-(CHOH)_x-(CH_2)_y-CONH(CH_2)_z-SH \quad (3)$$

wherein x represents a number from 0 to 5, y represents a number from 0 to 3, and z represents a number from 2 to 5, with the proviso that y and z do not simultaneously represent 0.

22. The method according to claim 7, wherein said oxidizing agent comprises at least one member selected from the group consisting of potassium bromate, sodium bromate, sodium perborate, and hydrogen peroxide.

23. The method according to claim 7, wherein the hair composition further comprises component (C):

a surfactant selected from the group consisting of an anionic surfactant, an amphoteric surfactant, a nonionic surfactant, and a cationic surfactant.

24. A hair treatment composition for imparting good manageability and excellent feeling to the touch to the hair upon finishing of permanent waving or hair dyeing treatment, comprising:

(A) a compound represented by the following formula (1):

$$R^1O-(PO)_n(EO)_m-R^2 \quad (1),$$

wherein $R_1$ represents a linear or branched $C_{8-12}$ alkyl or alkenyl group, PO represents a propyleneoxy group, EO represents an ethyleneoxy group, n represents an average addition mole number and is from 1.5 to 5.0, m represents an average addition mole number and is from 0 to 1.0, and $R^2$ represents a hydrogen atom or a methyl group, and (B) at least one member selected from the group consisting of keratin, a reducing agent, an oxidizing agent, an alkaline agent, and a dye for a hair dye; and $R^1OH$, wherein $R^1$ represents a linear or branched $C_{8-12}$ alkyl or alkenyl group, in an amount of 300 ppm or less.

25. A method of preparing of a permanent wave agent or a hair dye composition, comprising adding, to a hair composition comprising at least one of a permanent wave agent and a hair dye, the following component (A) and component (B):

(A) a compound represented by the following formula (1):

$$R^1O-(PO)_n(EO)_m-R^2 \quad (1),$$

wherein $R^1$ represents a linear or branched $C_{8-12}$ alkyl or alkenyl group, PO represents a propyleneoxy group, EO represents an ethyleneoxy group, n represents an average addition mole number and is from 1.5 to 5.0, m represents an average addition mole number and is from 0 to 1.0, and $R^2$ represents a hydrogen atom or a methyl group; and (B) at least one member selected from the group consisting of keratin, a reducing agent, an oxidizing agent, an alkaline agent, and a dye for hair dye, wherein the hair composition is for imparting good manageability and excellent feeling to the touch to the hair upon finishing of permanent waving or hair dyeing treatment, and wherein the hair composition further comprises $R^1OH$, wherein $R^1$ represents a linear or branched $C_{8-12}$ alkyl or alkenyl group, in an amount of 300 ppm or less.

* * * * *

UNITED STATES PATENT AND TRADEMARK OFFICE
CERTIFICATE OF CORRECTION

| | |
|---|---|
| PATENT NO. | : 8,349,024 B2 |
| APPLICATION NO. | : 13/387381 |
| DATED | : January 8, 2013 |
| INVENTOR(S) | : Juri Sata et al. |

It is certified that error appears in the above-identified patent and that said Letters Patent is hereby corrected as shown below:

In the Claims

Column 28 line 29 "wherein $R_1$ represents" should read --wherein $R^1$ represents--

Signed and Sealed this
Twenty-fifth Day of June, 2013

Teresa Stanek Rea
*Acting Director of the United States Patent and Trademark Office*